US00PP36705P3

(12) United States Plant Patent
Olesen

(10) Patent No.: US PP36,705 P3
(45) Date of Patent: May 27, 2025

(54) MINIATURE ROSE PLANT NAMED 'Poulty042'

(50) Latin Name: *Rosa hybrida*
Varietal Denomination: Poulty042

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/831,188

(22) Filed: Sep. 5, 2024

(65) Prior Publication Data

US 2025/0107467 P1 Mar. 27, 2025

(30) Foreign Application Priority Data

Sep. 22, 2023 (QZ) ..... PBR 20231981

(51) Int. Cl.
*A01H 5/02* (2018.01)
*A01H 6/74* (2018.01)

(52) U.S. Cl.
USPC ..... Plt./122

(58) Field of Classification Search
USPC ..... Plt./101, 116, 122
See application file for complete search history.

*Primary Examiner* — Susan McCormick Ewoldt

(57) ABSTRACT

A new garden rose plant of the Miniature class which has abundant, red flowers and attractive foliage. This new and distinct variety has shown to be uniform and stable in the resulting generations from asexual propagation.

2 Drawing Sheets

Botanical designation: *Rosa hybrida.*
Variety denomination: 'Poulty042'.

This application claims priority to Plant Breeder's Rights Application Number 2023/1981, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulty042', originated as a single seedling from the stated cross.

The new variety may be distinguished from its male pollen parent and female seed parent primarily by the following characteristics. The male pollen parent plant has very dark red flowers while the new variety has red flowers. The female seed parent grows to 40 cm in height while the new variety grows to 23 cm in height.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulty042' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulty042' was selected in the spring of 2015 by the inventor as a single plant from the progeny of the aforementioned hybridization.

Asexual reproduction of 'Poulty042' by rooted cuttings was first done by Mogens N. Olesen in the nursery in Fredensborg, Denmark in July 2015. This initial and other subsequent asexual propagations conducted in controlled environments have demonstrated that the characteristics of 'Poulty042' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulty042'.

Specifically illustrated in FIG. 1 of the drawings are open flowers viewed from above, underneath, and the side, petals detached revealing reproductive flower parts, sepals detached showing receptacle, and a flower bud.

Figure 1:
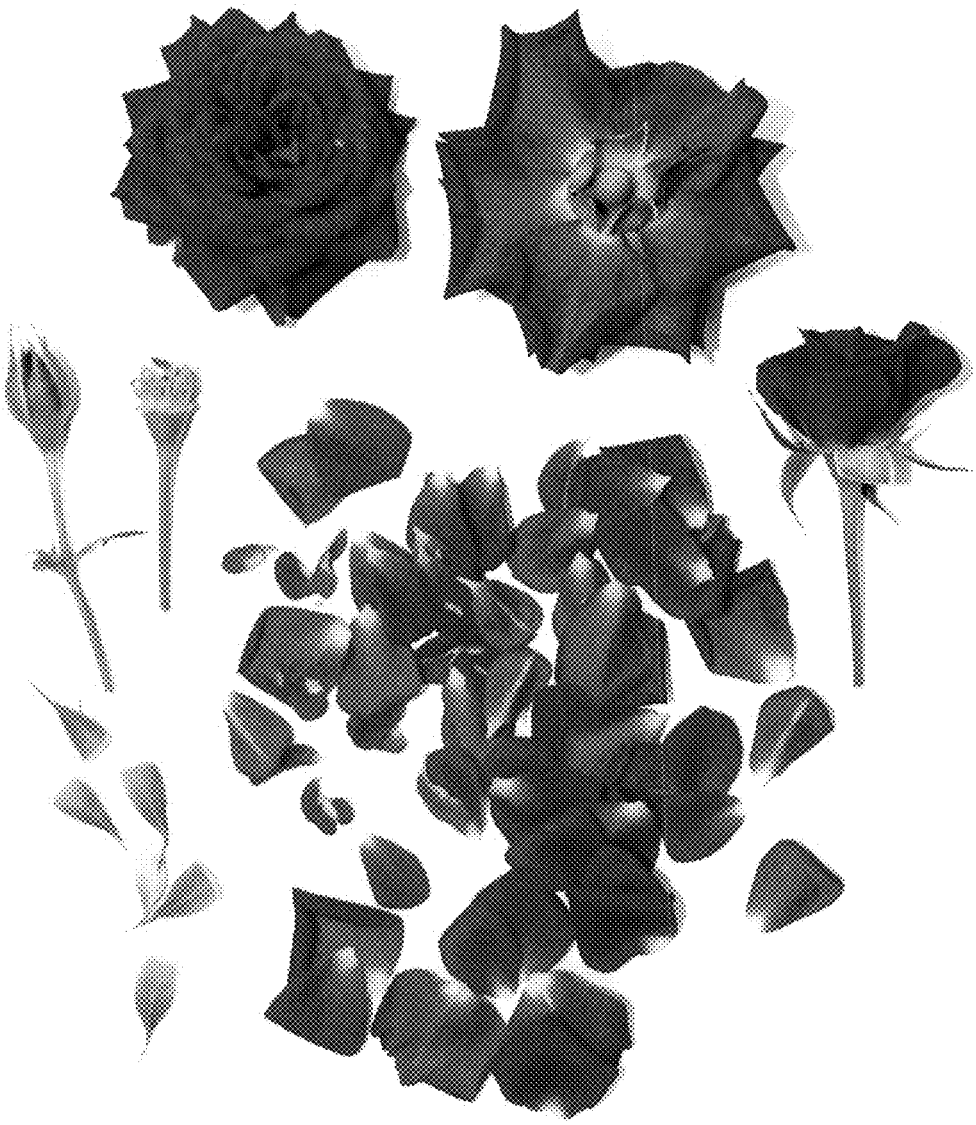
Figure 2:
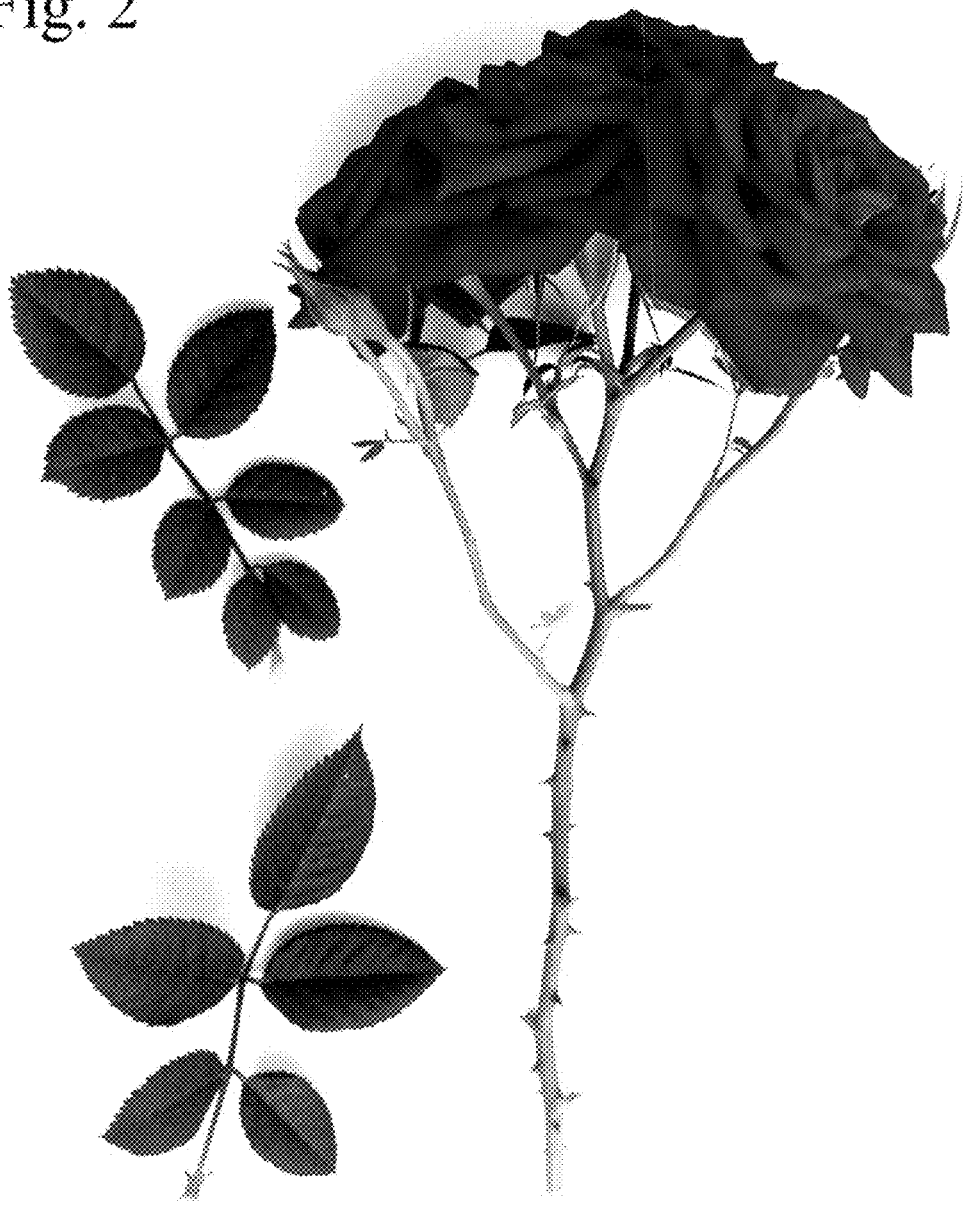

Specifically illustrated in FIG. 2 of the drawings is a cluster of open flowers on a bare stem exhibiting prickles, and leaves. Plants shown are 5 years of age.

DETAILED DESCRIPTION OF THE VARIETY

The following is a description of 'Poulty042', as observed in its growth in an indoor glasshouse nursery in Odense Denmark. Observed plants are 5 months of age, and were grown on their own roots in 17 cm pots. Color references are made using The Royal Horticultural Society (London, England) Colour Chart, 2001, except where common terms of color are used.

For a comparison, several physical characteristics of the rose variety 'Poulty011', U.S. Plant Pat. No. 25,296 are compared to the claimed plant. While 'Poulty042' has 60 flower petals, 'Poulty011' has 30 flower petals. The claimed plant has a flower diameter of 65 mm while 'Poulty011' has a flower diameter of 35 to 40 mm. Open flowers of 'Poulty042' are generally Red Group 53B in color while 'Poulty011' has a general tonality of Red Group 45B.

FLOWER AND FLOWER BUD

Blooming habit: Continuous.

Flower bud:

- *Size*.—Upon opening, 25 mm in length from base of receptacle to end of bud. Bud diameter is 14 mm.
- *Bud form*.—Ovoid.
- *Bud color*.—As sepals divide petals are Red-Purple Group 60C.
- *Sepal inner surface*.—Color: Yellow-Green Group 144C. Surface: Lightly pubescent.
- *Sepal outer surface*.—Color: Yellow-Green Group 144A. Texture: Smooth.
- *Sepal shape*.—Apex: Cirrhose. Base: Flat at union with receptacle.
- *Sepal margin*.—Margins have weak foliaceous appendages on three of the five sepals.
- *Sepal size*.—25 mm long, 10 mm wide.
- *Receptacle*.—Texture: Smooth. Size: 6 mm in height, 6 mm wide. Color: Yellow-Green Group 144A. Shape: Campanulate.
- *Pedicel*.—Surface: Smooth. Length: 20 mm. Diameter: 2 mm on average. Color: Yellow-Green Group 144A. Strength: Strong.
- *Peduncle*.—Length: About 20 to 50 mm. Diameter: 2 mm. Color: Yellow-Green Group 144A. Texture: Smooth.

Flower bud development: Flower buds are borne in clusters of 5 to 7 flower buds per stem. Development as a panicle.

Flower bloom:

- *Fragrance*.—Light floral
- *Duration*.—The blooms have a duration on the plant of approximately 21 days. Petals fall cleanly away from plant after flowers have fully matured.
- *Size*.—Flower diameter is generally 65 mm when open. Flower depth is 20 mm.
- *Flower shape*.—Star shaped from above. Rosette very double flower with many slightly overlapping petals of different sizes.
- *Shape of flower, side view*.—The upper portion is convex. The lower portion is flat.

Petalage: Under normal conditions, flowers have about 60 petals.

General tonality of flower: Open flowers are Red Group 53B.

Petal color:

- *Upon opening, outer petals*.—Upper surface: Red Group 53A. Lower surface: Red Group 53B.
- *Upon opening, inner petals*.—Upper surface: Red Group 53A. Lower surface: Red Group 53B.
- *Basal petal spots, upon opening*.—Upper surface: Yellow Group 3C. Lower surface: Yellow Group 3C.
- *After opening, outer petals*.—Upper surface: Red Group 53A to 53B. Lower surface: Red-Purple Group 60B.
- *After opening, inner petals*.—Upper surface: Red Group 53A to 53B. Lower surface: Red-Purple Group 60B.
- *Basal petal spots, after opening*.—Upper surface: Yellow Group 3C. Lower surface: Yellow Group 3C.

Petals:

- *Petal reflex*.—Bilaterally reflexed.
- *Margin*.—Entire and uniform. The apex has a small point at the center of the margin. Moderate undulations.
- *Shape*.—Broad and elliptic. Apex shape: Rounded. Base shape: Rounded.
- *Size*.—About 25 mm (l)×25 mm (w).
- *Texture*.—Smooth.
- *Thickness*.—Average.

Petaloids:

- *Size*.—10 mm (l) by 7 mm (w).
- *Quantity*.—About 12.
- *Shape*.—Elliptical with an acute base and rounded apices.
- *Color*.—Upper surface is Red Group 53A. Lower surface is Red Group 53B. Petaloid spot at basal zone Yellow Group 3C.

Reproductive flower parts:

- *Pollen*.—None observed.
- *Anthers*.—Size: 2 mm in length. Color: Yellow Group 10B. Quantity: 45 on average.
- *Filaments*.—Color: Yellow Group 11C with intonations of Red Group 39B. Length: 5 mm.
- *Pistils*.—Length: 5 mm. Quantity: 30 on average.
- *Stigmas*.—Color: Orange-White Group 159A.
- *Styles*.—Color: Green-White Group 157A with other intonations of Red-Purple Group 63A.
- *Location of stigmas*.—Inferior in location relative to the length of the filaments and the height of the anthers.
- *Hips*.—None Observed.

PLANT

Plant growth: Upright. Plants are about 23 cm in height, and 28 cm wide.

Stems:

- *Color of juvenile growth*.—Yellow-Green Group 144B.
- *Color of mature growth*.—Yellow-Green Group 144A.
- *Length*.—Canes are about 10 cm from the base of the plant to the flowering portion.
- *Diameter*.—About 4 mm.
- *Internodes*.—On mature canes about 25 mm between nodes.
- *Surface texture*.—Young wood: Smooth. Older wood: Smooth.

Long prickles:

- *Incidence*.—About 11 prickles per 10 cm of stem.
- *Size*.—Average length of prickles on mature stems is 5 mm.
- *Shape*.—Upper portion is linear. Lower portion is concave.
- *Color*.—Juvenile prickles: Greyed-Purple Group 184B. Mature prickles: Greyed-Purple Group 184A.

Plant foliage:

*Compound leaf.*—120 mm (l)×70 (w).

*Quantity*.—About 4 leaves per 10 cm of stem.

*Leaf bearing angle to the stem.*—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 8 mm long, 4 mm wide. Quantity: 2 per compound leaf. Shape: Linear, slightly broad based with outward extending apices. Margins: Finely serrated. Color: Yellow-Green Group 144A.

*Petiole*.—Length: About 15 mm. Diameter: 1.5 mm. Upper surface color: Yellow-Green Group 144A with intonations of Greyed-Purple Group 184A. Lower surface color: Yellow-Green Group 144A.

*Rachis*.—Length: 50 mm. Upper surface color: Yellow-Green Group 144A with intonations of Greyed-Purple Group 184A. Lower surface color: Yellow-Green Group 144A.

*Leaflet*.—Quantity: 5 or 7 leaflets. Margins: Serrated. Size: Terminal leaflets are about 46 mm long, 25 mm wide. Shape: Generally elliptical. Base: Rounded. Apex: Acute to mucronate. Texture: Smooth. Thickness: Average. Arrangement: Odd pinnate. Venation: Reticulate. lossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulty042' substantially as described and illustrated herein.

* * * * *